United States Patent [19]

Mase et al.

[11] Patent Number: 4,769,123
[45] Date of Patent: * Sep. 6, 1988

[54] ELECTROCHEMICAL DEVICE

[75] Inventors: Syunzo Mase, Tobishima; Shigeo Soejima, Nagoya, both of Japan

[73] Assignee: NGK Insulators, Ltd., Aichi, Japan

[*] Notice: The portion of the term of this patent subsequent to Mar. 3, 2004 has been disclaimed.

[21] Appl. No.: 922,474

[22] Filed: Oct. 23, 1986

[30] Foreign Application Priority Data

Oct. 26, 1985 [JP] Japan ................. 60-239828

[51] Int. Cl.$^4$ ................. G01N 27/46
[52] U.S. Cl. ................. 204/425; 204/426; 204/427
[58] Field of Search ................. 204/1 S, 421–429

[56] References Cited

U.S. PATENT DOCUMENTS

| 4,304,652 | 12/1981 | Chiba et al. | 204/425 |
| 4,384,935 | 5/1983 | DeJong | 204/426 |
| 4,496,455 | 1/1985 | Linder et al. | 204/425 |
| 4,502,939 | 3/1985 | Holfelder et al. | 204/426 |
| 4,505,806 | 3/1985 | Yamada | 204/426 |
| 4,505,807 | 3/1985 | Yamada | 204/426 |
| 4,568,443 | 2/1986 | Asayama et al. | 204/426 |
| 4,574,627 | 3/1986 | Sakurai et al. | 204/425 |
| 4,579,643 | 4/1986 | Mase et al. | 204/425 |
| 4,591,421 | 5/1986 | Yamada et al. | 204/425 |
| 4,647,364 | 3/1987 | Mase et al. | 204/425 |

Primary Examiner—T. Tung
Attorney, Agent, or Firm—Parkhurst & Oliff

[57] ABSTRACT

An electrochemical device for dealing with a measurement gas in an external measurement-gas space, including an electrochemical sensing element having a pumping cell and a sensing cell. The pumping cell has a first planar solid electrolyte body, and a first and a second electrode disposed on corresponding areas of opposite surfaces of the first solid electrolyte body. The sensing cell has a second planar solid electrolyte body, and a third and a fourth electrode disposed on the second solid electrolyte body. The sensing element has an internal measurement-gas space communicating with the external measurement-gas space, so that the measurement gas is introduced into the internal measurement-gas space with a predetermined diffusion resistance. The first and third electrodes are substantially exposed to the internal measurement-gas space. A reference gas is accommodated in a reference-gas space to which the second and fourth electrodes are substantially exposed to the reference-gas space. Thus, none of the electrodes are directly exposed to the external measurement-gas space.

16 Claims, 4 Drawing Sheets

ELECTROCHEMICAL DEVICE

BACKGROUND OF THE INVENTION

1. Field of the Invention

The present invention relates in general to an electrochemical device, and more particularly to improvements in an electrochemical device having a laminar structure, which includes an electrochemical cell employing a planar solid electrolyte body.

2. Discussion of the Prior Art

There has been known an electrochemical device which incorporates an electrochemical cell using a solid electrolyte. For example, such an electrochemical device is used as an oxygen sensor which utilizes zirconia ceramics or other oxygen-ion conductive materials, for determining the concentration of oxygen in an exhaust gas produced by an internal combustion engine of an automotive vehicle. The oxygen concentration is determined according to the principle of an oxygen concentration cell. Also known are electrochemical devices such as detectors or pumps which are adapted to detect hydrogen, nitrogen, carbon dioxide, etc. according to the principle of an oxygen concentration cell, like the oxygen sensor indicated above. Most of such known electrochemical devices use a solid electrolyte material which takes the form of a tubular body having an elongate bore closed at its one end. In view of relatively low productivity and high cost of manufacture of electrochemical devices using such a tubular solid electrolyte body, and from the standpoint of easy assembling of components of the electrochemical device, there has been an increasing trend in the recent years, of using an electrochemical device having a laminar structure wherein electrode layers are formed on a generally planar solid electrolyte body.

An electrochemical cell of such a planar electrochemical device generally constitutes a planar solid electrolyte substrate and at least one pair of electrodes. A common electrochemical device has two electrochemical cells which are superimposed on each other to form an integral laminar structure having an internal space (cavity) that communicates with an external space in which a gas to be measured (measurement gas) exists. The measurement gas is introduced into the internal space, with a predetermined diffusion resistance. One of the electrodes of each eletrochemical cell is exposed to the measurement gas in the internal space. One of the two electrochemical cells is used as a pumping cell which is operable to effect a pumping action to control the concentration of a given component of the measurement gas in the internal space. The other electrochemical cell is used as a sensing cell which is adapted to measure an electromotive force which is induced due to a differential in the concentration of the component to be measured, between the atmosphere in the internal space, and a suitable reference gas.

In such an electrochemical device of a laminar structure having an internal space, one of the pair of electrodes of each of the electrochemical pumping and sensing cells is exposed to the measurement gas in the internal space. The other electrode of the sensing cell is exposed to the reference gas, while the other electrode of the pumping cell is disposed so that it is exposed to the external measurement gas via a suitable porous protective layer. In the case where the measurement gas is "rich-burned" exhaust gases, the electrochemical device indicated above suffers from a problem that the outer pumping electrode of the pumping cell exposed to the exhaust gas tends to be deteriorated by corrosive or reductive gases such as carbon monoxide and hydrocarbon. Further, since the exhaust gases produced, for example, by a motor vehicle are in a chemically non-equilibrium and active state, the contact of such exhaust gases with the outer pumping electrode is likely to cause deterioration of the electrode due to dissolution or precipitation by the exhaust gases. In addition, the exhaust gases which flow at an extremely high velocity will cause vaporization of platinum which is commonly used as a material for the electrodes. The deterioration due to this platinum vaporization is not negligible. In the case of the exhaust gases other than the "rich-burned" exhaust gases, too, the outer pumping electrode tends to be contaminated due to deposition of finely divided particles of various substances contained in the exhaust gases.

SUMMARY OF THE INVENTION

It is therefore an object of the present invention to provide an electrochemical device having an improved construction suitable for minimizing the deterioration and contamination of the outer pumping electrode by the reductive gases to be measured.

According to the present invention, there is provided an electrochemical device for dealing with a measurement gas in an external measurement-gas space, comprising: (a) an electrochemical pumping cell having a first planar solid electrolyte body, and a first and second electrode which are disposed on corresponding areas of opposite major surfaces of the first planar solid electrolyte body; (b) an electrochemical sensing cell having a second planar solid electrolyte body, and a third and fourth electrode which are disposed on the second planar solid electrolyte body, the pumping cell cooperating with the sensing cell to constitute a laminar electrochemical sensing element; (c) means for defining an internal measurement-gas space in the electrochemical sensing element, the internal measurement-gas space communicating with the external measurement-gas space, so that the measurement gas is introduced from the external measurement-gas space into the internal measurement-gas space, with a predetermined diffusion resistance, the first electrode of the pumping cell and the third electrode of the sensing cell being substantially exposed to the internal measurement-gas space; and (d) means for defining a reference-gas space in the electrochemical sensing element, for accommodating a reference gas, the second electrode of the pumping cell and the fourth electrode of the sensing cell being substantially exposed to the reference-gas space.

In the electrochemical device of the present invention constructed as described above, the second electrode of the electrochemical pumping cell as well as the fourth electrode (reference electrode) of the sensing cell, is exposed to the reference-gas space formed in the electrochemical sensing element, so that the second electrode cooperates with the first electrode exposed to the internal measurement-gas space, to perform an electrochemical pumping operation. Thus, the second electrode is not exposed to the measurement gas in the external measurement-gas space, and is therefore protected from contamination or deterioration by the measurement gas, unlike the corresponding electrode used in a conventional electrochemical device.

In addition, the pumping impedance of the electrochemical pumping cell can be effectively reduced, since the first and second electrodes of the pumping cell are disposed on the corresponding areas of the opposite major surfaces of the first planar solid electrolyte body. Accordingly, the required pumping voltage to be applied between the two pumping electrodes to control the atmosphere within the internal measurement-gas space can be reduced. As a result, the deterioration of the first planar solid electrolyte body of the pumping cell can be effectively reduced, and the adverse effect of the pumping voltage on the sensing cell can be minimized.

According to one advantageous feature of the invention, the internal measurement-gas space consists of at least one flat space formed parallel to planes of the first and second planar solid electrolyte bodies, and may be formed between the first and second planar solid electrolyte bodies. Preferably, the internal measurement-gas space may consist of at least one thin flat space which has a thickness selected to provide the predetermined diffusion resistance, so that the at least one thin flat space itself may function as diffusion-resistance means. This thin flat space of spaces functioning as diffusion-resistance means may be adapted to communicate with the external measurement-gas space through a suitable inlet aperture formed in the sensing element. Alternatively, the thin flat space may have an inlet opening which opens directly to the external measurement-gas space. In either case, the third electrode of the sensing cell is preferably positioned a predetermined distance away from the inlet opening, or from the inlet communicating with the inlet aperture.

According to another advantageous feature of the invention, the electrochemical device comprises a porous layer having the predetermined diffusion resistance. This porous layaer is disposed in a portion of the internal measurement-gas space located near an inlet opening thereof through which the measurement gas is introduced, so that the first and third electrodes are exposed to the measurement gas through the porous layer.

According to a further advantageous feature of the invention, the internal measurement-gas space such as the thin flat space or spaces serving as diffusion-resistance means as indicated above, has ceramic bridging means for bridging a gap between two opposed surfaces which cooperate to define a thickness of the internal measurement-gas space. This ceramic bridging means therefore determines the thickness of the internal measurement-gas space which determines the diffusion resistance to the measurement gas.

According to a further feature of the invention, the first electrode of the electrochemical pumping cell and the third electrode of the electrochemical sensing cell are exposed to the internal measurement-gas space formed in the laminar sensing element which includes the two cells, such that the first and third electrodes face each other. Generally, the reference-gas space is held in communication with an ambient air.

According to a still further feature of the invention, the electrochemical sensing element including the pumping and sensing cells has an electrically insulating portion which has a high electrical resistance, and which electrically insulates a portion of the first planar solid electrolyte body contacting the second electrode of the pumping cell, from a portion of the first and/or second solid electrolyte body or bodies which contacts the fourth electrode of the sensing cell. This electrically insulating portion has a cutout adjacent to the first electrode of the pumping cell. The cutout permits electrical connection of the above-indicated portions of the solid electrolyte bodies which contact the second and fourth electrodes. This arrangement effectively minimizes the adverse effect of the resistance polarization by a pumping current between the first and second electrodes, on the measurement of an electromotive force induced between the third and fourth electrodes of the electrochemical sensing cell. Thus, the electrically insulating portion is effective to improve the detecting accuracy of the electrochemical device.

When the temperature of the measurement gas is not high enough to maintain the solid electrolyte bodies of the electrochemical element at a sufficiently high operating temperature, the sensing accuracy of the electrochemical device may not be satisfactorily high. Therefore, it is preferred that the electrochemical sensing element has a suitable heater for heating the solid electrolyte bodies to the desired operating temperature. The heater may be formed integrally with the sensing element, in contact with either one of the pumping or sensing cells.

BRIEF DESCRIPTION OF THE DRAWINGS

The foregoing and other objects, features and advantages of the present invention will become more apparent by reading the following detailed description of preferred embodiment of the invention, when considered in connection with the accompanying drawings, in which.

DETAILED DESCRIPTION OF THE INVENTION

To further illustrate the principle of the present invention, the preferred embodiments of the invention will be described in detail, by reference to the accompanying drawings.

Figure 1:
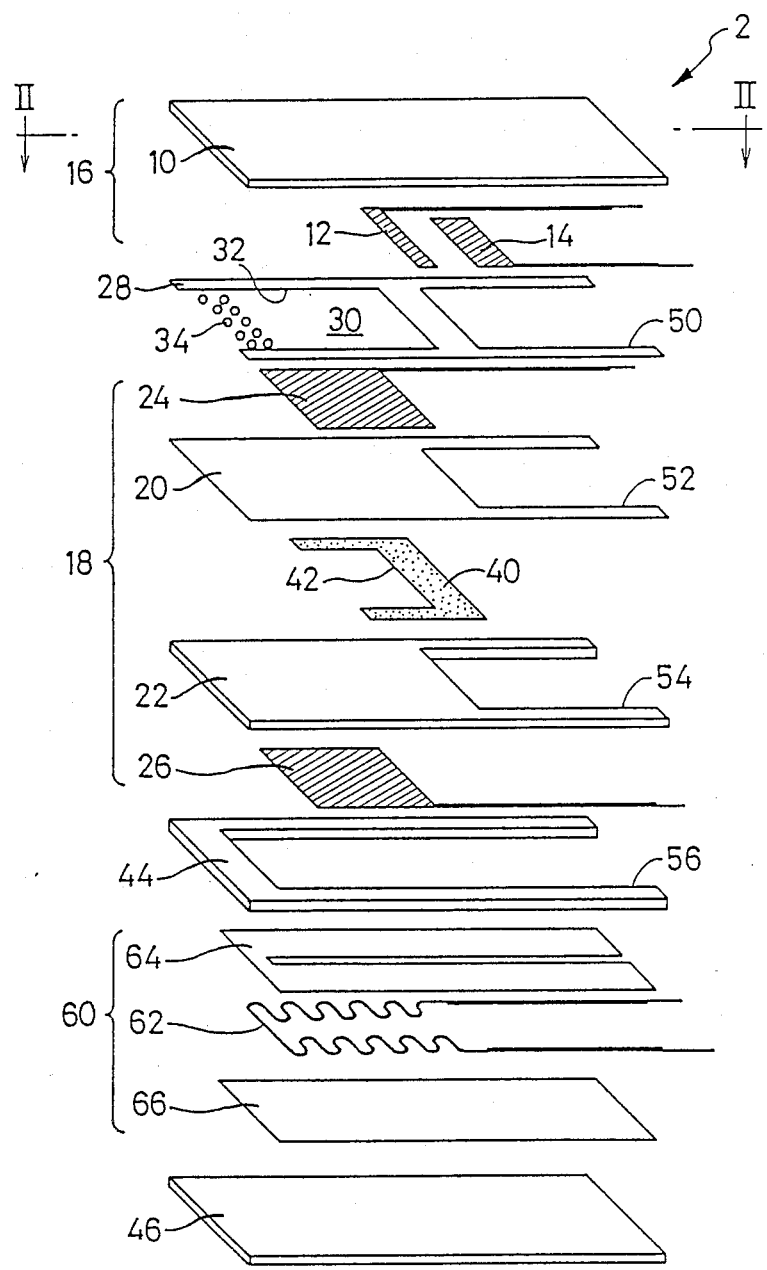
FIG. 1 is an exploded perspective view of a sensing element of one embodiment of the present invention in the form of an oxygen sensor.
Figure 2:
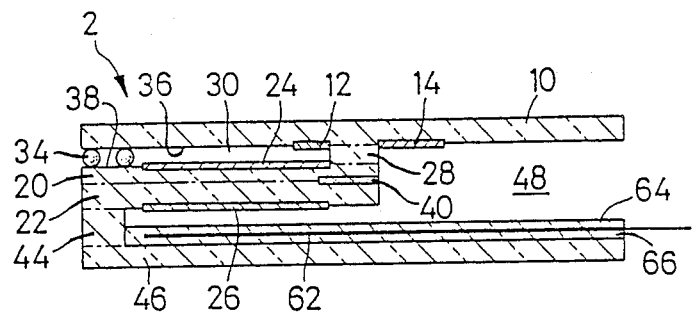
FIG. 2 is an elevational view in cross section taken along line II—II of FIG. 1.

Referring first to the exploded view of FIG. 1, and the longitudinal cross sectional view of FIG. 2, there is shown an electrochemical sensing element having a laminar structure according to one preferred arrangement of an electrochemical device of the invention, which is adapted to be used as an oxygen sensor. In the figures, reference numeral 10 designates a planar substrate made of zirconia ceramics or other solid electrolyte materials. This solid electroyte substrate is referred to as "second planar solid electrolyte body", if appropriate. A third electrode 12 (hereinafter referred to as "measuring electrode"), and a fourth electrode 14 (hereinafter referred to as "reference electrode"), are formed on the inner major surface of this solid electrolyte substrate 10, that is, on one of the opposite major surfaces of the substrate 10 which is not exposed to an exhaust gas or other gas to be measured (measurement gas), in the external space. The measuring and reference electrodes 12, 14 are made of platinum, for example, and are spaced apart from each other in the longitudinal direction of the substrate 10. The second solid electrolyte body 10, the measuring electrode 12, and the reference electrode 14 constitute an electrochemical sensing cell 16. The oxygen sensor also includes an electrochemical pumping cell 18 which includes a lamination of two solid electrolyte substrates 20, 22 similar to the second planar solid electrolyte body 10, a first electrode 24 (hereinafter referred to as "inner pumping electrode") and a second electrode 26 (hereinafter referred to as "outer pumping electrode"). The solid electrolyte lamination 20, 22 is referred to as "first planar solid electrolyte body", if appropriate. The inner and outer pumping electrodes 24, 26 have a porous structure made of platinum or other materials, and are formed on the opposite major surfaces of the first planar solid electrolyte body 20, 22, such that the two pumping electrodes 24, 26 are located at substantially the same positions.

Between the electrochemical sensing and pumping cells 16, 18, there is interposed an H-shaped spacer member 28 made of a suitable ceramic material. In this embodiment, the spacer member 28 is made of the same zirconia ceramic material as the first and second planar solid electrolyte bodies 10, 20–22. With the sensing and pumping cells 16, 18 superimposed with the H-shaped spacer member 28 sandwiched therebetween, there is formed an internal measurement-gas space in the form of a thin flat space 30, into which the measurement gas is introduced with a predetermined diffusion resistance. Thus, the measuring electrode 12 of the electrochemical sensing cell 16, and the inner pumping electrode 24 of the electrochemical pumping cell 18, are exposed to the atmosphere in the thin flat space 30. Described in greater detail, the H-shaped spacer member 28 has a cutout 32 which opens at one of its opposite longitudinal ends. The portion having the cutout 32 cooperates with the opposite surfaces of the solid electrolyte substrates 10, 20 of the pumping and sensing cells 16, 18, to define the thin flat space 30 which has a thickness substantially equal to the thickness of the spacer member 28 that is selected to provide the predetermined diffusion resistance. The thin flat space 30 has an inlet which opens to the external space (hereinafter referred to as "measurement-gas space"), at the longitudinal ends of the substrates 10, 20 corresponding to the open end of the cutout 32. The measuring electrode 12 of the sensing cell 16 is disposed so that it is exposed to the longitudinally innermost portion of the thin flat space 30.

In the thin flat space 30, there is provided a ceramic bridging member in the form of a plurality of ceramic grains 34 which are scattered near the open end or inlet of the space 30. This ceramic bridging member 34 bridges a gap between two opposed surfaces 36, 38 of the substrates 10, 20, as indicated in FIG. 2, thereby determining the thickness of the thin flat space 30 at its portion near the inlet opening.

As shown in FIG. 2, an electrically insulating layer 40 having a high electrical resistance is embedded in the first planar solid electrolyte body 20, 22, i.e., between the two solid electrolyte substrates 20, 22 of the electrochemical pumping cell 18. The insulating layer 40 provides a high-resistance area which electrically separates the portion of the solid electrolyte substrate 22 contacting the outer pumping electrode 26 of the pumping cell 18, from the solid electrolyte members 10, 28 of the sensing cell 16. More specifically, the electrically insulating layer 40 serves to prevent a flow of an electric current from the outer pumping electrode 26 of the pumping cell 18, via the spacer member 28, directly into the electrodes 12, 14 of the sensing cell 16. The insulating layer 40 has a rectangular cutout 42 which opens at its one side corresponding to the open end of the thin flat space 30. The insulating layer 40 is disposed so that the cutout 42 is aligned with the inner and outer pumping electrodes 24, 26 of the pumping cell 18, over a predetermined distance in the longitudinal direction of the sensing element. The cutout 42 is positioned adjacent to the inner pumping electrode 24.

On the side of the electrochemical pumping cell 18 on which the outer pumping electrode 26 is disposed, there are disposed a U-shaped spacer member 44 and a covering member 46 which are made of the same solid electrolyte material as the substrates 10, 20, 22. The electrochemical pumping cell 18 with the members 44, 46 formed thereon cooperates with the electrochemical sensing cell 16, to constitute an integral laminar structure of the electrochemical sensing element 2 (FIG. 2). This sensing element 2 has a reference-gas space in the form of an air space 48 which is defined by a cutout 50 formed in the H-shaped spacer member 28, cutouts 52, 54 formed respectively in the solid electrolyte substrates 20, 22, and a cutout 56 formed in the U-shaped spacer member 44, such that the cutouts 50, 52, 54 and 56 are covered by the solid electrolyte substrate 10 and the covering member 46. The air space 48 opens to the ambient air, at the end of the sensing element 2 remote from the other end at which the thin flat space 30 is open. Thus, the reference electrode 14 of the sensing cell 16 and the outer pumping electrode 26 of the pumping cell 18 are exposed to the ambient air in the air space 48.

Within the air space 48, there is provided an electric heater 60 formed in contact with the inner surface of the covering member 46. The heater 60 includes a heating element 62, and a pair of insulating layers 64, 66 which sandwich the heating element 62 therebetween. The insulating layers 64, 66 are made of an electrically insulating material such as zirconia or alumina having a high electrical resistance. More specifically, the heater 60 is positioned within the cutout 56 formed in the U-shaped spacer member 44, such that the insulating layer 66 is held in contact with the inner surface of the covering member 46.

In the present embodiment, the insulating layer 66 is formed from a porous layer made of alumina while the insulating layer 64 is formed from an air-tight layer made of zirconia having a high electrical resistance, in order to provide increased durability of the heating element 62 as well as improved electrical insulation of the electrochemical cells 16, 18 from the heating element 62.

In the electrochemical device having the thus constructed sensing element 2, a suitable value of DC voltage is applied between the inner and outer pumping electrodes 24, 26 of the electrochemical pumping cell 18 through suitable electrical leads, whereby oxygen is moved through the thickness of the first planar solid electrolyte body 20, 22, between the thin flat space 30 and the reference-gas or air space 48. Described in more detail, oxygen in the measurement gas in the thin flat space 30 is pumped out into the air space 48, or oxygen in the reference gas (ambient air) in the air space 48 is pumped into the thin flat space 30, by an amount proportional to the DC current flowing from the outer pumping electrode 26 toward the inner pumping electrode 24, or vice versa. In the meantime, an electromotive force is induced between the measuring and reference electrodes 12, 14 of the electrochemical sensing cell 16, due to a difference in the oxygen concentration between the atmosphere within the thin flat space 30, and the reference gas (air) in the air space 48. The induced electromotive force is applied, through suitable leads connected to the electrodes 12, 14, to an external device (not shown) for measuring the concentration of oxygen or unburned components contained in the measurement gas which is introduced into the thin flat space with a predetermined diffusion resistance.

The electrochemical device with the sensing element 2 operated as described above can be suitably used not only as a sensor for determining the oxygen concentration of the neutral exhaust gases which are produced as a result of combustion of an air-fuel mixture having the stochiometric air/fuel ratio, but also as a "lean-burn" or "rich-burned" sensor capable of dealing with "lean-burned" or "rich-burned" exhaust gases produced as a result of an air-fuel mixture having an air/fuel ratio higher or lower than the stoichiometric air/fuel ratio. Namely, the instant electrochemical device having an electrochemical pumping function provided by the pumping cell 18 is capable of controlling the oxygen concentration of the atmosphere adjacent to the measuring electrode 12 of the electrochemical sensing cell 16. This capability permits the device to handle the "lean-burned" gases, i.e., the exhaust gases produced in combustion of an air-rich air-fuel mixture having a higher oxygen concentration than the stoichiometric air-fuel mixture, or the "rich-burned" gases, i.e., the exhaust gases produced in combustion of a fuel-rich air-fuel mixture which has a lower oxygen concentration than the stoichiometric air-fuel mixture and which contains a large amount of unburned components. The electrochemical device is used to monitor the running condition of an engine producing the exhaust gases, by determining the concentration of oxygen or unburned components contained in the exhaust gases. In this connection, it is noted that the principle of the present invention can be more effectively practiced when the electrochemical device is used as a "rich-burn" sensor.

When the electrochemical device is used as a "rich-burn" sensor, the pump current (DC current) is applied so as to flow from the inner pumping electrode 24 toward the outer pumping electrode 26, in order to move a reference substance in the air space 48, namely, oxygen in the air space 48 communicating with the ambient air, toward the thin flat space 30. This direction of flow of the pump current is opposite to that when the device is used as a "lean-burn" sensor. Therefore, in the "rich-burn" sensor, the unburned components of the exhaust gases which have diffused through the thin flat space 30 with a predetermined diffusion resistance, are burned adjacent to the inner pumping electrode 24, due to a reaction of the unburned components with oxygen which has been moved from the air space 48 (from the outer pumping electrode 26) to the thin flat space 30 (to the inner pumping electrode 24). A change of the atmosphere within thin flat space 30 due to the above reaction, is detected as a change in the electromotive force induced between the two electrodes of the electrochemical sensing cell 16, that is, between the measuring and reference electrodes 12, 14. Thus, the electrochemical device can determine the amount of the unburned components contained in the exhaust gases, and consequently can determine the combustion condition of an air-fuel mixture (A/F ratio of the mixture) which gives the exhaust gases which have the detected amount of unburned components.

The "rich-burn" exhaust gases in the external measurement-gas are corrosive or reductive gases containing carbon monoxide, hydrocarbon, etc. However, the outer pumping electrode 26 of the pumping cell 18 is not exposed to such reductive exhaust gases, but exposed to the atmosphere within the reference-gas space or air space 48. Accordingly, the outer pumping electrode 26 is perfectly protected from contamination or deterioration due to such reductive exhaust gases. Further, the inner pumping electrode 24 of the pumping cell 18, and the measuring electrode 12 of the sensing cell 16, which are exposed to the atmosphere in the thin flat space 30 communicating with the external measurement gas, will not be deteriorated since the atmosphere in the space 30 is controlled by the pumping action of the pumping cell 18, so that the atmosphere is held substantially neutral or stoichiometric, that is, neither "rich-burned" nor "lean-burned" exhaust gases.

The inner pumping electrode 24 and the measuring electrode 12 will not be deteriorated if the atmosphere within the thin flat space 30 is not held neutral, because these electrodes are disposed at the innermost portion of the thin flat space 30 in the longitudinal direction of the sensing element 2. Described more particularly, the inner pumping electrode 24 and the measuring electrode 12 are exposed to the atmosphere in the innermost portion of the space 30. This atmosphere is the measurement gas that has introduced into the thin flat space 30, and diffused through the space 30 with the predetermined diffusion resistance. During the diffusion of the measurement gas through the thin flat space 30, the molecules of the gaseous components collide with the walls of the space 30, or collide with each other, whereby the atmosphere existing in the innermost portion of the space 30 is almost in a state of chemical equilibrium. Further, there exists substantially no flow of the atmosphere in the innermost portion of the thin flat space 30. Therefore, the electrodes 12, 24 exposed to the innermost portion of the thin flat space 30 are effectively protected from dissolution, precipitation or evaporation by the gaseous components.

In the illustrated embodiment, the opposed flat surfaces 36, 38 defining the thickness of the thin flat space 30 are bridged by the plurality of ceramic grains 34 disposed near the inlet opening of the space 30, whereby the thickness of the open end portion of the space 30 is substantially determined by the ceramic grains 34. The ceramic grains 34 serve to prevent otherwise possible deformation of the thin flat space 30 during manufacture of the sensing element 2, and contribute to maintaining the predetermined diffusion resistance of the thin flat space 30. Thus, the provision of the ceramic bridging member 34 results in a minimum variation in the diffusion resistance of the thin flat space 30, from one sensing element to another. In other words, the thickness of the thin flat space 30, particularly its thickness near the open end or inlet, is properly controlled by the size of the ceramic grains 34 which bridge the opposed flat surfaces 36, 38 of the solid electrolyte substrates 10, 20 defining the space 30. Hence, the diffusion resistance determined by the thickness of the thin flat space 30 can be suitably controlled by the size of the ceramic grains 34.

While the ceramic bridging member used in the illustrated embodiment takes the form of grains 34, it is possible to use other forms, such as planar rectangular members of suitable dimensions arranged in spaced-apart relation with each other in the thin flat space 30, or a porous layer which disposed near the inlet of the space 30, so as to provide a suitable diffusion resistance to the measurement gas. In any case, the thin flat space 30 having a ceramic bridging member (34) disposed therein must provide a predetermined diffusion resistance to the measurement gas which diffuses from the external measurement-gas space into the thin flat space 30.

As described above, the electrochemical sensing cell 16 of the instant electrochemical element 2 is electrically insulated from the electrochemical pumping cell 18 by the electrically insulating layer 40. Therefore, the sensing cell 16 is effectively protected from an adverse effect of resistance polarization by the pumping cell 18.

The instant electrochemical element 2 is heated to an optimum operating temperature by the built-in heater 60, so that the electrochemical device or oxygen sensor can operate in a reliable manner, with the solid electrolyte substrates 10, 20, 22 of the sensing and pumping cells 16, 18 held at the desired elevated temperatures, even while the temperature of the measurement gas is low. In addition, the built-in heater 60 accommodated within the air space 48 will not suffer from flake-off or deterioration which would take place if the heater was exposed directly to the measurement gas in the external space outside the sensing element 2.

The solid electrolyte substrates 10, 20, 22 which constitute major essential parts of the sensing and pumping cells 16, 18 of the instant sensing element 2 are preferably made of zirconia ceramics, as previously described. However, these substrates may be made of aluminum nitride, $SrCeO_3$, solid solutions of $Bi_2O_3$ and rare earth oxides, or $La_{1-x}Ca_xYO_{3-\alpha}$.

The electrochemical element 2 may be prepared in a suitable known process. For instance, unfired layers for the electrodes 12, 14, 24, 26 and their electrical leads are screen-printed on green sheets of the solid electrolyte substrates 10, 20, 22. The green sheets are superimposed on each other, with an unfired layer for the H-shaped spacer member 28 sandwiched therebetween, to form an unfired assembly of the sensing and pumping cells 16, 18. Unfired layers or green sheets for the other members such as the U-shaped spacer member 44 and air-tight covering member 46 are superimposed on the unfired assembly of the cells 16, 18. The obtained unfired laminar structure is then fired to produce the sensing element 2.

In the case where the electrochemical sensing element 2 is prepared by co-firing the unfired layers or geen sheets, it is desirable to co-fire the unfired layers of the electrodes 12, 14, 24, 26 and their leads. In this case, the electrodes and the leads are preferably formed by a screen-printing technique, using a paste whose major component is selected from the platinum group which includes platinum, palladium, rhodium, iridium, ruthenium and osmium. To avoid flake-off or peel-off or breakage of the electrodes and their leads, it is desirable to add powders of zirconia, yttria, alumina or other suitable ceramic materials, to the materials of the paste. With the addition of such ceramic materials, the adhesion of the electrodes and leads to the contacting solid electrolyte layers is improved.

The ceramic grains 34 bridging the opposed surfaces 36, 38 of the thin flat space 30 are advantageously made of the same material as the solid electrolyte substrates 10, 20 which have the opposed surfaces 36, 38. Preferably, the ceramic grains 34 have a diameter which is equal to or slightly larger than the desired thickness of the thin flat space 30. As previously indicated, the ceramic grains 34 may be replaced by ceramic members having other shapes, for example, ceramic strips. In any case, the ceramic bridging member is disposed in the thin flat space 30, so that the space 30 has a predetermined diffusion resistance to the measurement gas.

While one form of the electrochemical device of the present invention has been described and illustrated, it is to be understood that the invention is not limited to the embodiment described above, but may be otherwise embodied. For example, the invention may be modified as shown in FIGS. 3 and 4.

Figure 4:
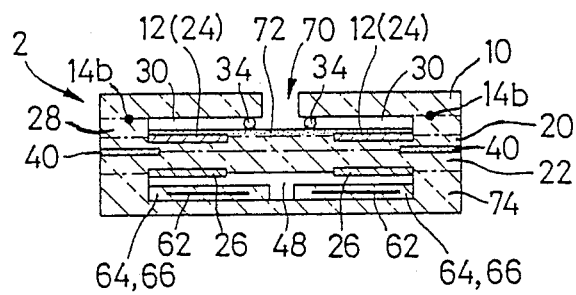
FIGS. 4 and 6 are cross sectional views taken along line IV—IV and line VI—VI of FIGS. 3 and 5, respectively.
Figure 3:
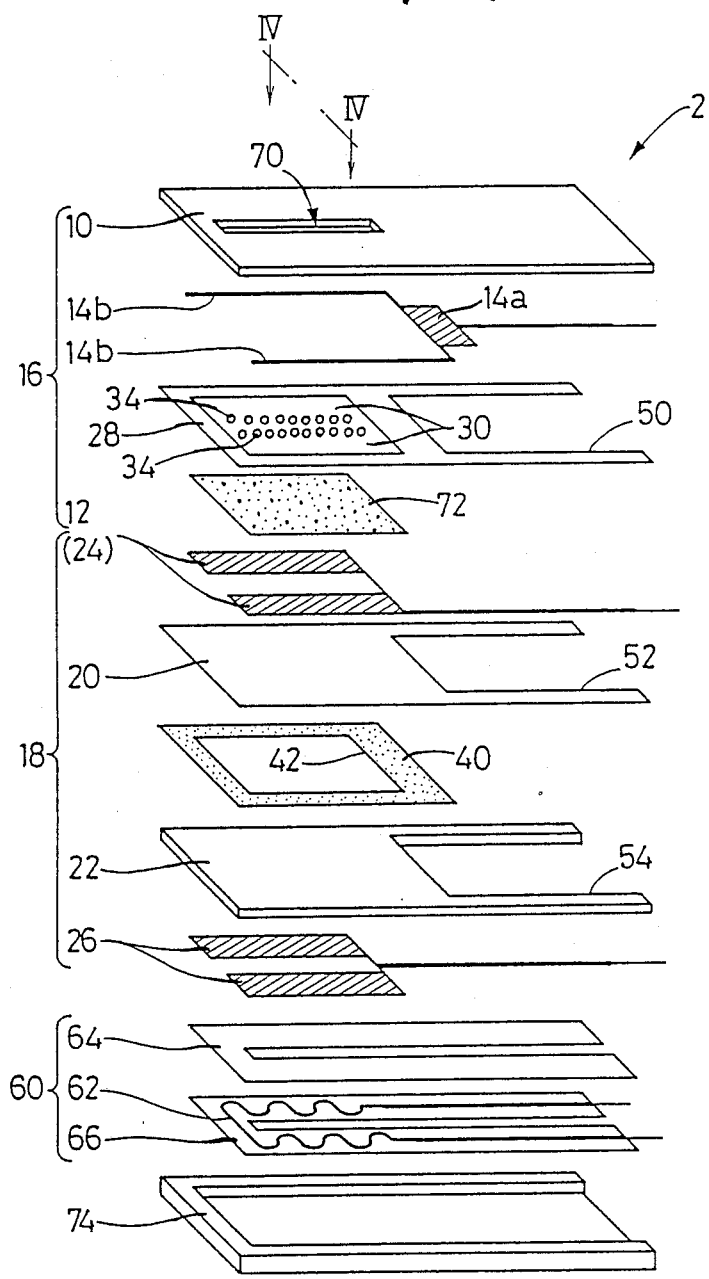
FIGS. 3 and 5 are views corresponding to that of FIG. 1, showing sensing elements of oxygen sensors according to other embodiments of electrochemical devices of the invention.

The modified embodiment of FIGS. 3 and 4 uses an oxygen sensing element (electrochemical sensing element 2) wherein the thin flat space 30 having a predetermined diffusion resistance is held in communication with the external measurement-gas space via an inlet aperture 70. This inlet aperture 70 is an elongate rectangular slot formed through the second planar solid electrolyte body 10, so as to extend in the longitudinal direction of the element 2, such that the rectangular slot 70 divides the thin flat space 30 into two sections extending parallel to the slot 70. Two parallel rows of ceramic bridging grains 34, 34 are disposed within the thin flat space 30, so as to extend parallel to the slot 70, and near the open ends or inlets of the two sections of the space 30 on the opposite sides of the slot 70. The ceramic grains 34 bridge a gap between the opposed surfaces defining the thickness of the thin flat space 30, as indicated in FIG. 4. Thus, the thickness of the thin flat space 30 is determined by the diameter of the ceramic grains 34.

The reference electrode 14 of the sensing cell 16 used in the present modified embodiment 4 consists of a planar portion 14a and a pair of parallel wire-like portions 14b, both portions 14a, 14b being formed on the inner surface of the solid electrolyte substrate 10. The planar portion 14a is exposed to the reference-gas space or air space 48, while the wire-like portions 14b extend from the planar portion 14a in the longitudinal direction of the sensing element 2, toward the longitudinal end of the sensing element 2 on the side of the thin flat space 30. The wire-like portions 14b are positioned on the opposite sides of the thin flat space 30, and have the same potential as the planar portion 14a. The measuring electrode 12 of the sensing cell 16, which also serves as the inner pumping electrode 24 of the pumping cell 18, is made up of two spaced-apart, electrically connected parallel sections formed on the solid electrolyte substrate 20. These two parallel sections of the electrode 12 (24) are alinged with the portions of the two sections of the thin flat space 30 which are remote from the elongate inlet aperture or slot 70 in the direction across the length of the sensing element 2. The electrode 12 (24) is covered by a porous protective layer 72 made of a suitable ceramic material.

In the present modified embodiment, the electrochemical sensing cell 16 is constituted by the substrate 10 and spacer member 28 both made of a solid electrolyte, the two-part measuring electrode 12, and the reference electrode 14 (which consists of the planar portion 14a and the wire-like portions 14b). On the other hand, the electrochemical pumping cell 18 is constituted by the two solid electrolyte substrates 20, 22, the two-part inner pumping electrode 24 (serving also as the measuring electrode 12) on the substrate 20, and the outer pumping electrodes 26 which consists of two parallel sections on the substrate 22, in aligned relation with the corresponding two parallel sections of the inner pumping electrodes 24.

On the outer side of the pumping cell 18 on which the outer pumping electrode 26 is disposed, there is formed a covering member 74 which is an integral combination of the spacer member 44 and the covering member 46 used in the preceding embodiment. This covering member 74 cooperates with the other members 10, 28, 20 and 22 to define the reference-gas space in the form of the air space 48. The outer pumping electrode 26 of the pumping cell 18 and the planar portion 14a of the reference electrode 14 of the sensing cell 16 are exposed to the reference gas within air space 48. In the air space 48, the electric heater 60 having the same construction as that used in the preceding embodiment is accommodated in contact with the inner surface of the covering member 74.

The thus constructed electrochemical element 2 provides the same advantages as discussed in connection with the preceding embodiment. In addition, the present modified embodiment is simplified in construction because a single electrode is commonly used as the measuring electrode 12 of the sensing cell 16 and the inner pumping electrode 24 of the pumping cell 18. The wire-like portions 14b of the reference electrode 14, which are disposed near the measuring electrode 12, function to reduce the impedance between the electrodes 12, 14, thereby enhancing the detecting accuracy of the sensing element 2.

The present electrochemical sensing element 2 is adapted to measure an electromotive force between the reference electrode 14, and the measuring electrode 12 which is also the inner pumping electrode 24. This arrangement would have a greater tendency of the sensing cell 16 being affected by the resistance polarization of the two electrodes 24, 26 of the pumping cell 18. However, the influence of the resistance polarization of the pumping cell 18 is effectively minimized by the electrically insulating layer 40, which electrically separates the portion of the solid electrolyte substrate 22 contacting the outer pumping electrode, from the portions of the solid electrolyte members 10, 28, 20 on the side of the sensing cell 16. Accordingly, the insulating layer 40 serves to assure an improved accuracy of measurement of the electromotive force induced in the sensing cell 16.

In the instant arrangement, the inlet aperture 70 may be used as diffusion-resistance means for providing a predetermined resistance to the diffusion of the measurement gas into the thin flat space 30. In this case, the inlet aperture 70 may cooperate with the thin flat space 30 to provide diffusion-resistance means. Alternatively, the inlet aperture 70 may be formed so as to provide a diffusion resistance larger than that of the thin flat space 30. In this latter instance, the thin flat space 30 may be formed, without a need to precisely control its diffusion resistance, i.e., without giving considerations to its diffusion resistance.

Figure 6:
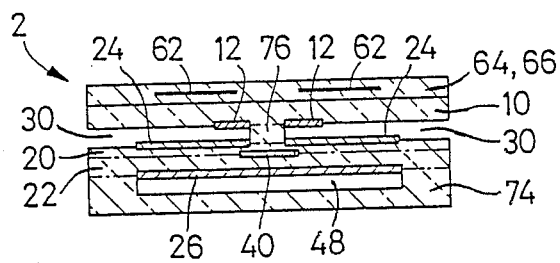
Figure 5:
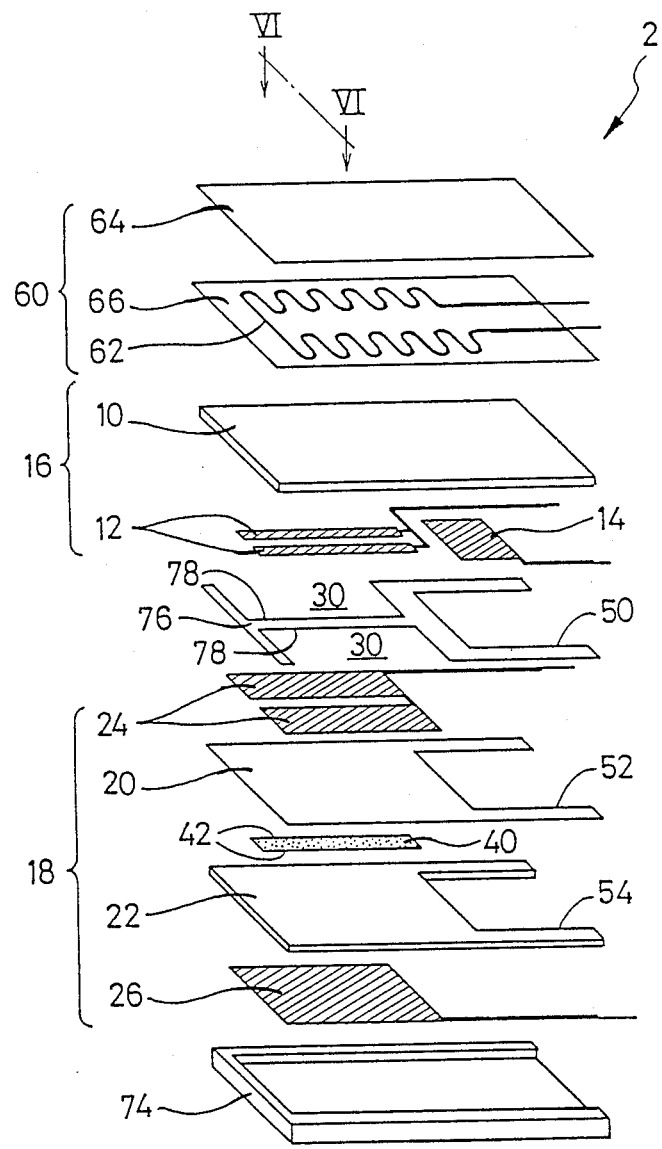

A further modified arrangement of the electrochemical sensing element 2 for an oxygen sensor is illustrated in FIGS. 5 and 6, which is characterized by two separate thin flat spaces 30 which open in the opposite side surfaces of the element 2. The total length of opening of the thin flat spaces 30 is made greater than that of the thin flat space 30 provided in the previous two embodiments. This means an improved operating response of the sensing element 2 of the present embodiment. Described in more detail, a spacer member 76 has two mutually independent rectangular cutouts 78, which open in the opposite lateral sides of the spacer member 76. With this spacer member 76 sandwiched between the sensing and pumping cells 16, 18, the two thin flat spaces 30 corresponding to the cutouts 78 are formed, such that these thin flat spaces 30 open in the opposite side surfaces of the sensing element 2. The two spaced-apart parallel sections of the measuring electrode 12 of the sensing cell 16 are located at the innermost portions of the corresponding thin flat spaces 30 which are remote from their inlets at the opposite side surfaces of the element 2. Similarly, the two spaced-apart parallel sections of the inner pumping electrode 24 of the pumping cell 18 are located at the innermost portions of the thin flat spaces 30. Thus, the measuring and inner pumping electrodes 12, 24 are exposed to the measurement gas which has been introduced into the thin flat spaces 30 through their open ends, with a predetermined diffusion resistance.

In the oxygen sensor (electrochemical device) using the electrochemical element 2 constructed as described above, the measuring and reference electrodes 12, 14 of the sensing cell 16, and the inner and outer pumping electrodes 24, 26 of the pumping cell 18, are all accommodated in the thin flat spaces 30 or air space 48, and are thus protected from direct exposure to the measurement gas in the external space. Therefore, the instant embodiment also enjoys the advantages according to the principle of the invention, as previously discussed. In the instant embodiment, the electric heater 60 is provided on the outer surface of the sensing element 16, in contact with the solid electrolyte substrate 10, in order to maintain the sensing element 2 at its operating temperature, for reliable operation of the device.

The concept of the present invention is also applicable to an electrochemical device wherein an internal measurement-gas space (cavity) formed in the electrochemical sensing element is held in communication with the external measurement-gas space, through a diffusion-resistance means in the form of a pin hole or orifice which has a predetermined diffusion resistance, as disclosed in Japanese Patent Application No. 58-218400 the priority of which is claimed in U.S. Pat. No. 4,579,643.

While the several different preferred embodiments of the invention have been described and illustrated, it is to be understood that the invention is not limited thereto, but various changes, modifications and improvements which may occur to those skilled in the art, may be made in the invention, without departing from the spirit and scope of the invention.

Although the electrochemical device according to the present invention is suitably used as a "rich-burn" sensor for "rich-burned" exhaust gases, it may be utilized not only as a sensor for dealing with the exhaust gases produced as a result of combustion of air-fuel mixtures having an air/fuel ratio in the neighborhood of the stoichiometric level, but also as a "lean-burn" sensor for dealing with the "lean-burned" exhaust gases produced in combustion of fuel-lean air-fuel mixtures. Further, the instant electrochemical device can be used as other sensors, detectors or controllers adapted to detect nitrogen, carbon dioxides, hydrogen and other components of a fluid which are associated with electrode reaction.

As is apparent from the foregoing description, the electrochemical device according to this invention incorporates a laminar electrochemical sensing element including an electrochemical pumping cell and an electrochemical sensing cell. The electrochemical sensing element is constructed such that a first electrode of the pumping cell and a third electrode of the sensing cell are exposed to a thin flat space into which an external measurement gas is introduced with a predetermined diffusion resistance, while a second electrode of the pumping cell and a fourth electrode of the sensing cell are exposed to a reference-gas space also formed in the sensing element. The first and second electrodes of the pumping cell are disposed on the corresponding portions of the opposite surfaces of a planar solid electrolyte body. Unlike the outer pumping electrode used in a known device, the second electrode of the pumping cell is not exposed to the measurement gas in the external measurement-gas space, and is therefore effectively protected from contamination or deterioration by the measurement gas. Further, the pumping impedance of the pumping cell is made small, for lowering the pumping voltage applied to the pumping cell to effect an electrochemical pumping operation. Thus, the solid electrolyte body is effectively protected from deterioration by the pumping voltage, while at the same time the adverse effect of the pumping voltage on the sensing cell is minimized. These are considered to be industrially significant features of the present invention.

What is claimed is:

1. An electrochemical device for measuring a measurement gas in an external measurement-gas space, comprising:
    an electrochemical pumping cell having a first planar solid electrolyte body and a first and second electrode which are disposed on opposite major surfaces of said first planar solid electrolyte body;
    an electrochemical sensing cell having a second planar solid electrolyte body and a third and fourth electrode which are disposed on said second planar solid electrolyte body, in substantially the same plane which is parallel to a plane of said second planar solid electrolyte body, said pumping cell cooperating with said sensing cell to constitute a laminar electrochemical sensing element;
    means for defining an internal measurement-gas space in said electrochemical sensing element, said internal measurement-gas space communicating with said external measurement-gas space, so that the measurement gas is introduced from said external measurement-gas space into said internal measurement-gas space, with a predetermined diffusion resistance, said first electrode of said pumping cell and said third electrode of said sensing cell communicating with said internal measurement-gas space; and
    means for defining a reference-gas space in said electrochemical sensing element, for accommodating a reference gas, said second electrode of said pumping cell and said fourth electrode of said sensing cell being located within said reference-gas space.

2. The electrochemical device of claim 1, wherein said internal measurement-gas space consists of at least one flat space formed parallel to planes of said first and second planar solid electrolyte bodies.

3. The electrochemical device of claim 1, wherein said internal measurement-gas space is formed between said first and second planar solid electrolyte bodies.

4. The electrochemical device of claim 1, further comprising a plurality of ceramic grains disposed in a portion of said internal measurement-gas space, thereby defining an inlet opening thereof through which said measurement gas is introduced.

5. The electrochemical device of claim 1, wherein said internal measurement-gas space consists of at least one thin flat space which has a thickness selected to provide said predetermined diffusion resistance, said at least one thin flat space functioning as a diffusion-resistance means.

6. The electrochemical device of claim 1, further comprising means for defining an inlet aperture through which said internal measurement-gas space communicates with said external measurement-gas space.

7. The electrochemical device of claim 1, wherein said internal measurement-gas space has an inlet opening which opens directly to said external measurement-gas space, said third electrode of said electrochemical sensing cell being positioned a predetermined distance away from said inlet opening of said internal measurement-gas space.

8. The electrochemical device of claim 1, further comprising ceramic bridging means for bridging a gap between two opposed surfaces defining a thickness of said internal measurement-gas space, thereby determining the thickness of said internal measurement-gas space.

9. The electrochemical device of claim 1, wherein said first electrode and said third electrode communicate with said internal measurement-gas space such that said first and third electrodes face each other.

10. The electrochemical device of claim 1, wherein said reference-gas space has a portion which is located in substantially the same plane as said internal measurement-gas space.

11. The electrochemical device of claim 1, wherein said reference-gas space communicates with an ambient air.

12. The electrochemical device of claim 1, wherein said first electrode of said pumping cell and said third electrode of said sensing cell are constituted by a single common electrode.

13. The electrochemical device of claim 1, wherein said electrochemical sensing element has an electrically insulating portion having a high electrical resistance, said electrically insulating portion electrically insulating a portion of said first planar solid electrolyte body contacting said second electrode of the pumping cell from a portion of said second planar solid electrolyte body which contacts said fourth electrode of said sensing cell, thereby substantially electrically insulating said second electrode from said fourth electrode, said electrically insulating portion having a cutout adjacent to said first electrode of said pumping element, said cutout permitting electrical connection of said portions of the solid electrolyte bodies which contact said second and first electrodes.

14. The electrochemical device of claim 1, wherein said electrochemical sensing element has a heater formed integrally in contact with one of said pumping and sensing cells, for heating said sensing element to an operating temperature thereof.

15. The electrochemical device of claim 1, wherein said third and fourth electrodes of said sensing cell are disposed on one of opposite major surfaces of said second planar solid electrolyte body.

16. The electrochemical device of claim 1, wherein said fourth electrode consists of a plurality of portions electrically connected to each other, one of said portions being embedded in said second planar solid electrolyte body.

* * * * *